United States Patent [19]
Chikama

[11] Patent Number: 5,271,382
[45] Date of Patent: Dec. 21, 1993

[54] BENDING DEVICE

[75] Inventor: Toshio Chikama, Tokyo, Japan

[73] Assignee: Kabushiki Kaisha Machida Seisakusho, Tokyo, Japan

[21] Appl. No.: 910,460

[22] Filed: Jul. 8, 1992

[30] Foreign Application Priority Data

Jul. 24, 1991 [JP] Japan .................. 3-207438

[51] Int. Cl.$^5$ .................. A61B 1/00
[52] U.S. Cl. .................. 128/4; 138/120
[58] Field of Search .......... 128/4, 6, 7, 8, 10, 128/11; 138/120, 118; 604/95

[56] References Cited

U.S. PATENT DOCUMENTS

| | | | |
|---|---|---|---|
| 832,523 | 10/1906 | Andersson | 138/120 |
| 3,162,214 | 12/1964 | Bazinet, Jr. | 138/120 |
| 3,190,286 | 6/1965 | Stokes | |
| 3,929,164 | 12/1975 | Richter | 138/120 |
| 4,108,211 | 8/1978 | Tanaka | 138/120 |
| 4,432,349 | 2/1984 | Oshiro | |
| 4,703,135 | 10/1987 | Magnani et al. | 138/120 X |
| 4,726,355 | 2/1988 | Okada | 128/4 |
| 4,773,395 | 9/1988 | Suzuki et al. | 128/4 |
| 4,790,294 | 12/1988 | Allred, III et al. | |

FOREIGN PATENT DOCUMENTS 3704815 8/1987 Fed. Rep. of Germany .
61-188701 11/1986 Japan .

*Primary Examiner*—Richard J. Apley
*Assistant Examiner*—Karen Jalbert
*Attorney, Agent, or Firm*—Fish & Richardson

[57] ABSTRACT

An elongate bending device for use in an endoscope or the like includes a number of segments which are arranged in a row along a longitudinal axis of the bending device and are pivotally connected to one another, and at least one operating wire extending through the segments along the longitudinal axis of the bending device. That portion of the inner peripheral surface of the segment along which the operating wire extends serves as a wire guide surface portion. This wire surface guide portion forms an inwardly convex, continuous curved line. The distance between the wire guide surface portion and the longitudinal axis of the bending device is increasing progressively from a central portion of the wire surface guide portion toward the opposite ends of the wire surface guide portion.

9 Claims, 5 Drawing Sheets

BENDING DEVICE

BACKGROUND OF THE INVENTION

This invention relates generally to a bending device for use in an endoscope or the like, and more particularly to an improved bending device designed not to cut an operating wire passing through the interior of the bending device.

Figure 13:
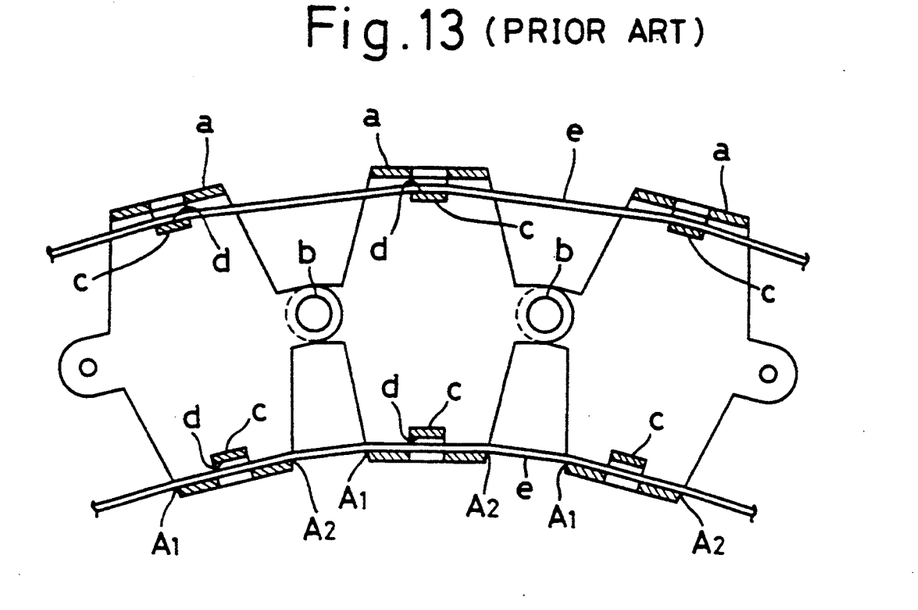
FIG. 13 is a cross-sectional view showing the conventional bending device.

A bending device for an endoscope as shown in FIG. 13 comprises a number of cylindrical segments a arranged in a row. The left end of each segment a is pivotally connected by pintles b to the right end of the left adjoining segment a at two points circumferentially spaced 180° from each other. Each segment a has a pair of inwardly-directed, stamped guide portions c circumferentially spaced 90° from the pintles b. Operating wires e are passed through the guide portions c.

In the above construction, when the lower operating wire e is pulled while the upper operating wire e is loosened, each segment a is pivotally moved relative to its adjoining segment a, so that the bending device is bent or curved downwardly. In contrast, when the upper operating wire e is pulled, the bending device is bent upwardly.

In the above bending device, when the operating wire e is cut off, it is impossible to bend the bending device. Therefore, it is desired to reduce the possibility cutting of the operating wire and thus prolonging the lifetime of the operating wire.

Figure 14:
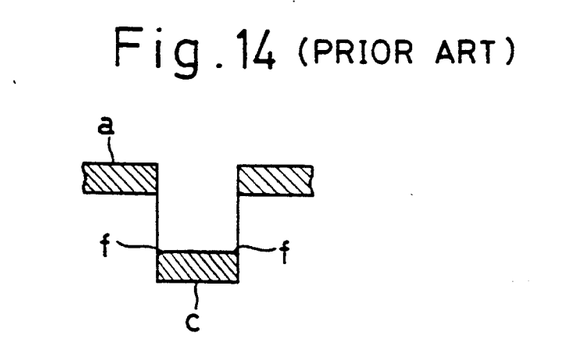
FIG. 14 is an enlarged view showing one example of guide portion of the conventional bending device.
Figure 15:
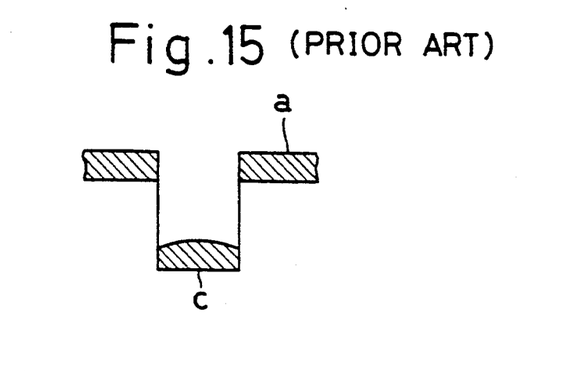
FIG. 15 is an enlarged view showing another example of guide portion of the conventional bending device.

In a bending device disclosed in Japanese Laid-Open Utility Model Application No. 61-188701, opposite ends of a guide portion c are chamfered as at f as shown in FIG. 14. Alternatively, the diameter d of a hole in the guide portion c is increasing progressively from its central portion toward the opposite ends thereof, as shown in FIG. 15. However, such arrangements have hardly contributed to the prevention of the cutting of the operating wire. The reasons for this will now be described.

As shown in FIG. 13, to bend the bending device downwards, the lower operating wire e is pulled while the upper operating wire e is loosened. Therefore, the operating wire e that may be cut off is the lower one. Therefore, the lower operating wire e will not be in contact with the guide portions c. Therefore, the configurations of the guide portion c as shown in FIGS. 14 and 15 are insignificant.

The pulled operating wire e is bent by opposite ends $A_1$ and $A_2$ of that portion (i.e., wire guide surface portion) of the inner peripheral surface of each segment a along which this operating wire is extended. Since this wire guide surface portion extends straight, the pulling force of the operating wire e concentrates on the opposite ends $A_1$ and $A_2$ of the wire guide surface portion, so that the contact pressure on the operating wire with these opposite ends becomes very high. It is quite possible that the operating wire e may be cut off as a result of the repeated bending of the operating wire and the rubbing of the operating wire with the opposite ends $A_1$ and $A_2$ of the segments a under a high contact pressure.

Referring to other related art, U.S. Pat. Nos. 3,190,286 and 4,432,349 describe a technique in which opposite ends of each wire guide surface portion with which a pulled operating wire is contacted are chamfered. However, the wire guide surface portion except for its opposite ends is extended straight, and this straight portion does not bear the pulling force of the operating wire at all. Therefore, the pressure of contact between the opposite ends of the straight portion of the wire guide surface portion and the operating wire becomes high, and as a result the lifetime of the operating wire cannot be prolonged.

SUMMARY OF THE INVENTION

It is an object of this invention to provide a bending device in which the lifetime of an operating wire is prolonged.

According to one aspect of the present invention, there is provided a bending device comprising:

(a) a number of segments arranged in a row along a longitudinal axis of the bending device, any two adjacent ones of the segments being pivotally connected together, the segment having an arcuate portion disposed around the longitudinal axis of the bending device, and guide means being provided on an inner side of the arcuate portion; and (b) an operating wire extending through the segments along the longitudinal axis of the bending device, the operating wire having a distal end substantially fixed relative to a foremost one of the segments, the operating wire being guided by the guide means, the bending device being bent when a proximal end of the operating wire is subjected to a pulling force, and that portion of an inner peripheral surface of the segment along which the operating wire extends serving as a wire guide surface portion;

(c) the wire guide surface portion forming an inwardly-convex, continuous curved line, the distance between the wire guide surface portion and the longitudinal axis of the bending device increasing progressively from a central portion of the wire guide surface portion toward opposite ends of the wire guide surface portion.

According to another aspect of the invention, there is provided a bending device comprising:

(a) a number of segments arranged in a row along a longitudinal axis of the bending device, any two adjacent ones of the segments being pivotally connected together, the segment including a tubular portion, the segment having a pair of first connecting portions extending axially from one end of the tubular portion, the first connecting portions being circumferentially spaced 180° from each other, the segment having a pair of second connecting portions extending axially from the other end of the tubular portion, the second connecting portions being circumferentially spaced 180° from each other, and being circumferentially spaced 90° from the first connecting portions, the pair of first connecting portions of any one of the segments overlap the pair of second connecting portions of its adjoining segment, respectively, and being pivotally connected by respective pintles to these second connecting portions, respectively, and four guide means being provided on an inner side of the segment, and being disposed in registry respectively with the first and second connecting portions in a direction of the circumference of the segment; and (b) four operating wires extending through the segments along the longitudinal axis of the bending device, the four operating wires having their distal ends substantially fixed relative to a foremost one of the segments, the four operating wires being guided by the four guide means, respectively, the bending device being bent when a proximal end of each of the operating wires is subjected to a pulling force;

(c) inner peripheral surfaces of the tubular portions of any two adjacent ones of the segments cooperating with an inner surface of an inner one of the overlapped first and second connecting portions to form a substantially continuous wire guide surface portion along which the operating wire extends, the wire guide surface portion forming an inwardly convex, substantially continuous curved line, and the distance between the wire guide surface portion and the longitudinal axis of the bending device increasing progressively from a central portion of the wire guide surface portion toward opposite ends of the wire guide surface portion.

DESCRIPTION OF THE PREFERRED EMBODIMENTS

Figure 1:
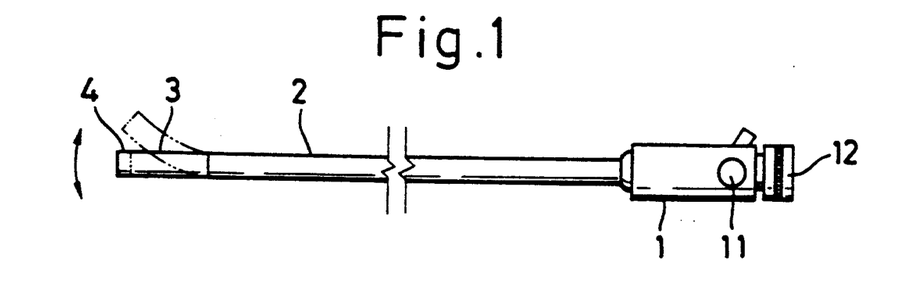
FIG. 1 is a view showing an overall construction of an endoscope provided with a bending device according to the present invention.

Preferred embodiments of the present invention will now be described with reference to the drawings. FIGS. 1 to 7 show one preferred embodiment of the present invention. As shown in FIG. 1, an endoscope in this embodiment comprises a body 1, an insertion portion 2 extending from a front end of the body 1, a bending portion 3 extending from a distal end of the insertion portion 2, and a rigid tip 4 provided at a distal end of the bending portion 3. A manipulation handle 11 and an ocular portion 12 are mounted on the body 1. An illumination window and an inspection window (both of which are not shown) are provided at an end face of the tip 4. When the manipulation handle 11 is angularly moved, the bending portion 3 is bent via operating wires 5 (later described), thereby changing the direction of the tip 4. By doing so, a desired portion can be viewed or observed from the ocular portion 12. An optical system interconnecting the inspection window and the ocular portion 12, as well as an optical system interconnecting the illumination window and a light source device, is well known in the art, and therefore will not be described here.

Figure 2:
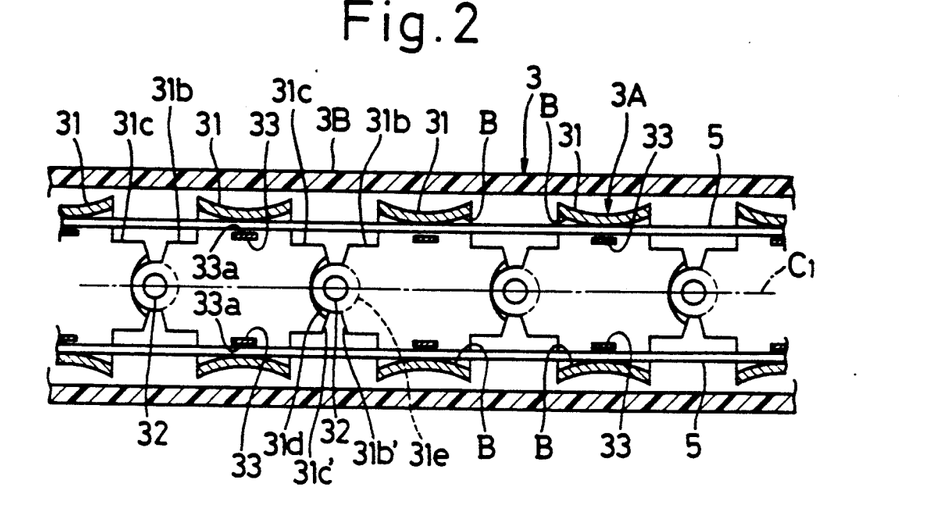
FIG. 2 is a cross-sectional view showing the bending device in its straight condition.

As shown in FIG. 2, the bending portion 3 comprises an elongate bending device 3A, and a protective tube 3B of a resin covering the bending device 3A. The bending device 3A comprises a number of segments 31 arranged in a row along its longitudinal axis (centerline) $C_1$, any two adjacent ones of the segments 31 being pivotally connected together to provide an articulation construction.

Figure 5:
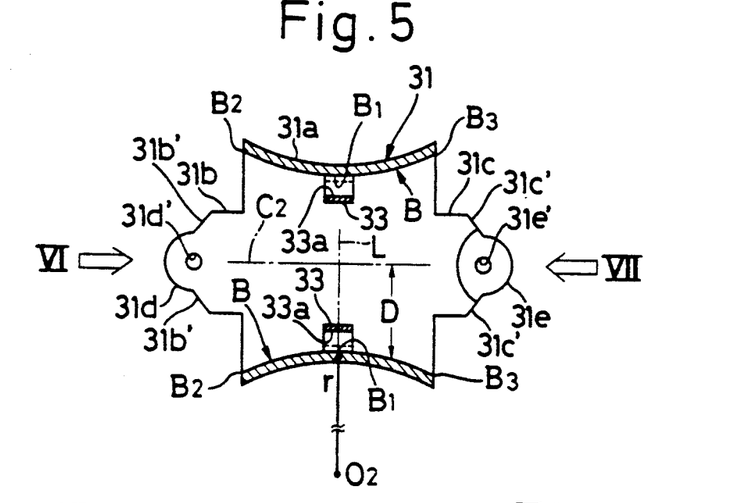
FIG. 5 is an enlarged cross-sectional view of the segment.
Figure 6:
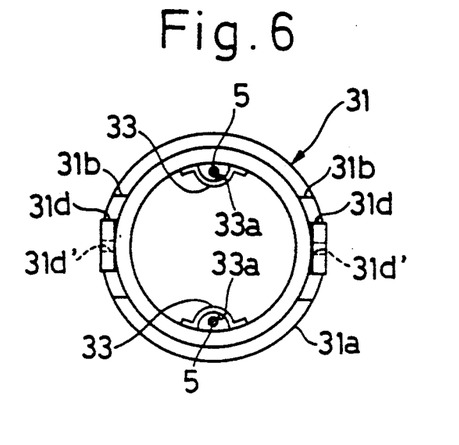
FIG. 6 is a view as seen in the direction of arrow VI of FIG. 5.
Figure 7:
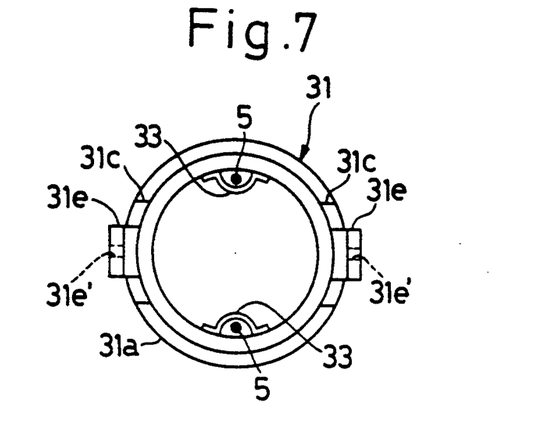
FIG. 7 is a view as seen in the direction of arrow VII of FIG. 5.

As best shown in FIGS. 5 to 7, each segment 31 includes a tubular portion 31a of a circular cross-section. An axis $C_2$ of the tubular portion 31a coincides with the axis $C_1$ of the bending device 3A. A pair of projections 31b are formed on one end of the tubular portion 31a, and are circumferentially spaced 180° from each other. The pair of projections 31b extend parallel to the axis $C_2$ of the tubular portion 31a. A pair of projections 31c are formed on the other end of the tubular portion 31a, and extend parallel to the axis $C_2$ of the tubular portion 31a. The pair of projections 31c being disposed in registry with the pair of projections 31b, respectively, in the direction of the circumference of the tubular portion 31a. A connecting portion 31d having a hole 31d' is formed on the distal end of each projection 31b. The connecting portion 31d is disposed on an imaginary line of extension of the projection 31b. A connecting portion 31e having a hole 31e' is formed on the distal end of each projection 31c. The connecting portion 31e is offset radially outwardly from the projection 31c by an amount corresponding to the thickness of the projection 31c.

As shown in FIG. 2, in the above bending device 3A, the connecting portions 31d of any one of the segments 31 overlap the connecting portions 31e of the left-adjoining segment 31, respectively. Each pair of the thus overlapped connecting portions 31d and 31e are pivotally connected together by a rivet (pintle) 32 extending through their holes 31d' and 31e'.

A pair of semi-cylindrical guide members (guide means) 33 are fixedly mounted respectively on diametrically-opposite portions of the inner peripheral surface of the segment 31 which are circumferentially spaced 180° from each other and are also circumferentially spaced 90° from the projections 31b and 31c. The pair of guide members 33 are disposed centrally of the axial length of the segment 31, and have their respective axes extending parallel to the axis of the segment 31. A guide hole 33a is defined by the guide member 33 and the inner peripheral surface of the segment 31. The pair of operating wires 5 are passed respectively through the pair of guide holes 33a provided at each segment 31. One ends of the pair of operating wires 5 are fixedly secured to either the rigid tip 4 or the foremost segment 31, and are circumferentially spaced 180° from each other. The other ends of the pair of operating wires 5 are connected to a pulley (not shown) mounted within the body 1. This pulley is connected to the manipulation handle 11 via a shaft (not shown) extending through the wall of the body 1. When the manipulation handle 11 is angularly moved in one direction, one of the operating wires 5 is pulled while the other operating wire 5 is loosened. As a result, a series of segments 31 are pivotally moved relative to one another, so that the bending device 3A and hence the bending portion 3 are bent.

When the bending device 3A is fully bent, shoulders 31b' of the projections 31b of any one of the segments 31 abut respectively against shoulders 31c' of the projections 31c of its adjoining segment 31. Therefore, the maximum amount of bending of the bending device 3A is determined by this abutment.

The tubular portion 31a of the segment 31 has a uniform thickness, and has a circular cross-sectional shape over the entire length thereof, and the diameter of the tubular portion 31a is increasing progressively from its central portion toward its opposite ends. As shown in FIG. 5, a line, defined by the intersection between the inner peripheral surface of the tubular portion 31a and an imaginary plane including the axis $C_2$ of the tubular portion 31a, is curved line convex toward the axis $C_2$. In this embodiment, this curved line is an arc, and its radius of curvature is indicated by r. Therefore, those portions of the inner peripheral surface of the tubular portion 31a along which the pair of operating wires 5 are extended, respectively, (that is, a pair of wire guide surface portions B), are also in the shape of an arc whose radius of curvature is r. The center $O_2$ (see FIG. 5) of a circle part of which is defined by the arc with the radius r of curvature is disposed on a line L passing centrally of the axial length of the tubular portion 31a, and extends perpendicularly to the axis $C_2$ of the tubular portion 31a. With this arrangement, the distance D between the wire guide surface portion B and the axis $C_2$ of the tubular portion 31a is increasingly progressively from the center $B_1$ toward the opposite ends $B_2$ and $B_3$.

Figure 3:
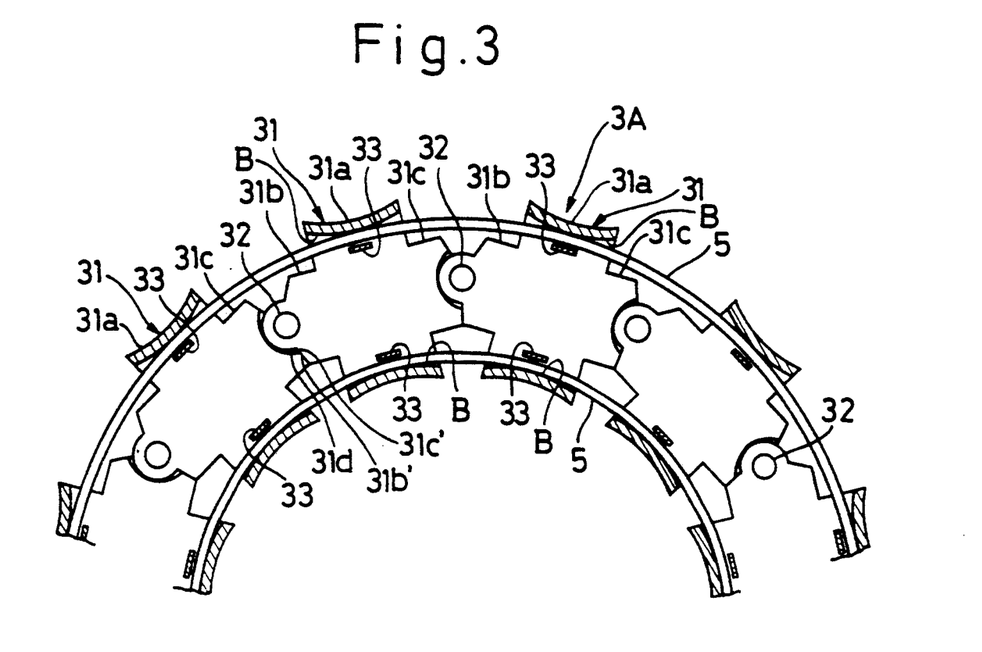
FIG. 3 is a cross-sectional view showing the bending device in its fully-bent condition.
Figure 4:
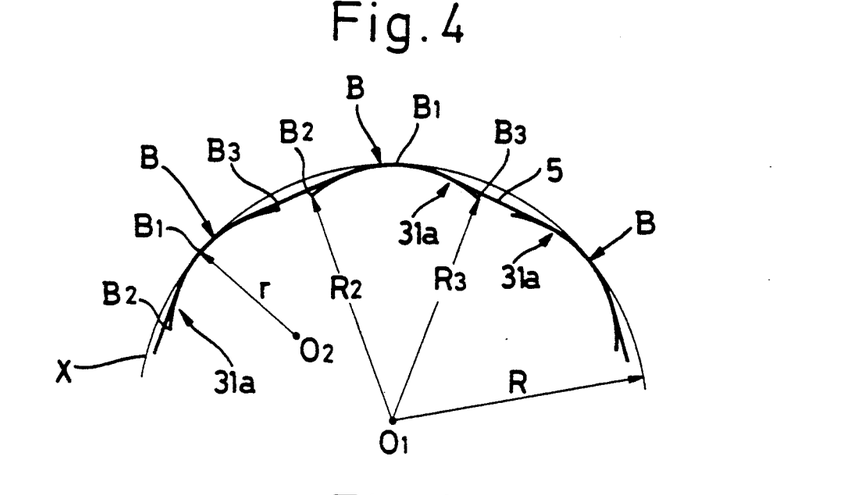
FIG. 4 is a view showing the relation between wire guide surface portions on inner peripheral surfaces of segments and an operating wire in the fully-bent condition of the bending device.

Here, let's assume that the lower operating wire 5 is pulled to bend the bending device 3A downwardly to the maximum degree, as shown in FIGS. 3 and 4. At this time, if the distance between the center $O_1$ of curvature of the bending device 3A (see FIG. 4) and the center $B_1$ of each lower wire guide surface portion B (in other words, the radius of curvature of a circle X on which the centers $B_1$ of the wire guide surface portions B of a number of segments 31 lie) is indicated by R, then the radius r of curvature of the wire guide surface portion B satisfies the following formula:

$$r < R$$

The center $B_1$ of the wire guide surface portion B, the center $O_1$ of the radius R of curvature, and the center $O_2$ of the radius r of curvature are disposed generally on a common line. It will readily be appreciated from the above formula that the distance R between the center $O_1$ and the center $B_1$ of the wire guide surface portion B is greater than the distance $R_2$ between the center $O_1$ and one end $B_2$ of the wire guide surface portion B and also than the distance $R_3$ between the center $O_1$ and the other end $B_3$ of the wire guide surface portion B. Therefore, the lower operating wire (the pulled operating wire) 5 is held out of contact with the opposite ends $B_2$ and $B_3$ of the wire guide surface portion B even when the bending device 3A is bent to the maximum degree, as shown in FIG. 4. The section of contact of the wire guide surface portion B with the operating wire 5 (The center of this contact section lies generally at the center $B_1$ of the wire guide surface portion B) becomes longer as the degree of bending of the bending device 3A becomes high. Since the wire guide surface portion B receives the pulling force of the operating wire 5 generally uniformly over the entire length of this contact section, the contact pressure will not become extremely high at any localized region of the wire guide surface portion B. Therefore, the operating wire 5 will not be repeatedly bent by the ends $B_2$ and $B_3$, and will be rubbed by the wire guide surface portions B under a low contact pressure. As a result, the lifetime of the operating wire 5 can be prolonged.

Other preferred embodiments of the present invention will now be described. In the preceding embodiment, the maximum amount of bending of the bending device is determined by the abutment of the shoulders 31b' of the projections 31b against the shoulders 31c' of the projections 31c; however, in an embodiment shown in FIG. 8, the maximum bending amount is determined by the abutment of opposed ends of tubular portions 31a of two adjacent segments 31 against each other. In this case, also, if R > r is satisfied, the operating wire 5 in a pulled condition is always held out of contact with the opposite ends $B_2$ and $B_3$ of each wire guide surface portion B.

Figure 8:
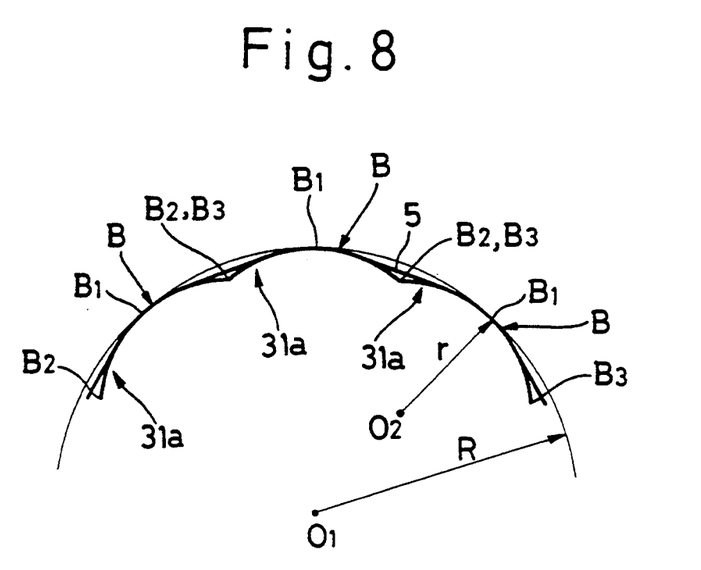
FIGS. 8 and 9 are views similar to FIG. 4, but show modified forms of the invention, respectively.
Figure 9:
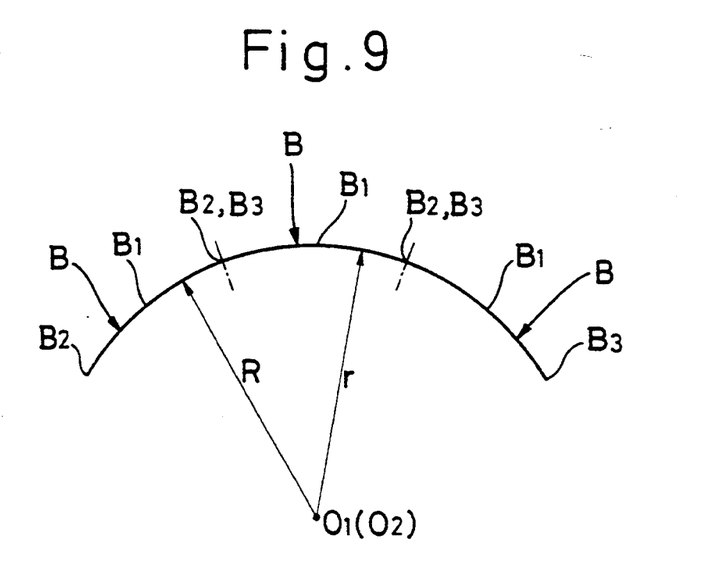

In an embodiment shown in FIG. 9, the maximum bending amount is determined as in the embodiment of FIG. 8. In this embodiment, R = r is satisfied. When a bending device is bent to the maximum degree, the operating wire (not shown) in a pulled condition is held in contact with each wire guide surface portion B over an entire length thereof, and therefore is contacted with opposite ends $B_2$ and $B_3$. However, since the operating wire extends in a direction tangent to each wire guide surface portion B, the pressure of contact between the operating wire and the wire guide surface portion B is low at the opposite ends $B_2$ and $B_3$.

Figure 10:
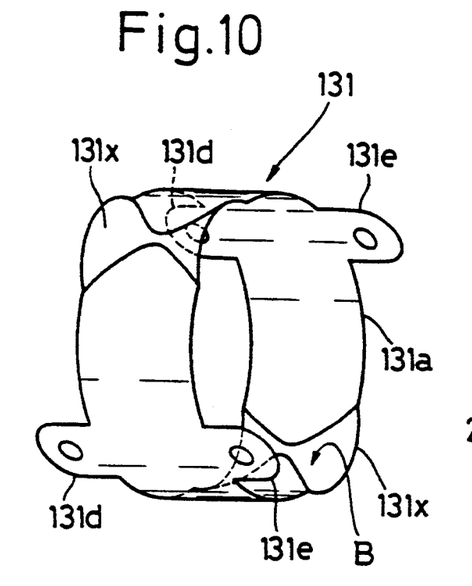
FIG. 10 is a perspective view of a modified segment.

A segment 131 shown in FIG. 10 includes a tubular portion 131a of a generally cylindrical shape having a uniform thickness. As in the preceding embodiments, a pair of connecting portions 131d are formed on one end of the tubular portion 131a, and a pair of connecting portions 131e are formed on the other end of the tubular portion 131a, and guide members (not shown) are mounted on the inner surface of the tubular portion 131a. In this embodiment, a pair of expanded portions 131x are formed respectively on those portions of the tubular portion 131a disposed in registry respectively with the guide members in the circumferential direction. The distance between the expanded portion 131x and the axis of the tubular portion 131a is increasing progressively from the central portion of the expanded portion 131x toward the opposite ends of the expanded portion 131x. The inner surface of the expanded portion 131x serves as a wire guide surface portion B similar to that described in the above embodiments.

Figure 11:
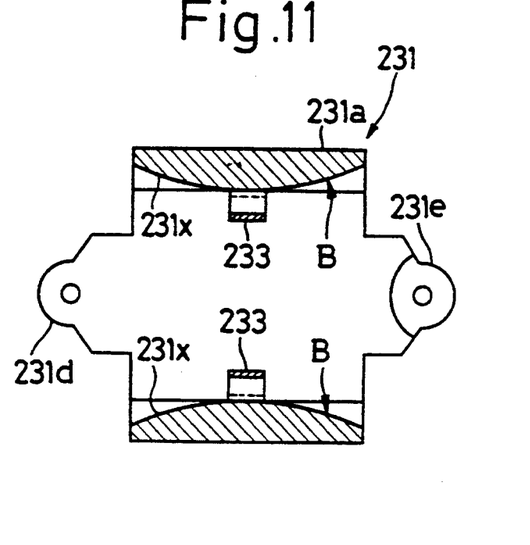
FIG. 11 is a cross-sectional view of another modified segment.

A segment 231 shown in FIG. 11 includes a tubular portion 231a of a generally cylindrical shape. As in the above embodiments, a pair of connecting portions 231d are formed on one end of the tubular portion 231a, and a pair of connecting portions 231e are formed on the other end of the tubular portion 231a, and guide members 233 are mounted on the inner surface of the tubular portion 231a. In this embodiment, the outer peripheral surface of the tubular portion 231a is a complete cylindrical surface. A pair of grooves 231x are formed respectively in those portions of the inner peripheral surface of the tubular portion 231a disposed in registry respectively with the guide members 233, the grooves 231x extending axially of the tubular portion 231a. The bottom surface of the groove 231x serves as a wire guide surface portion B similar to that described in the above embodiments.

Figure 12:
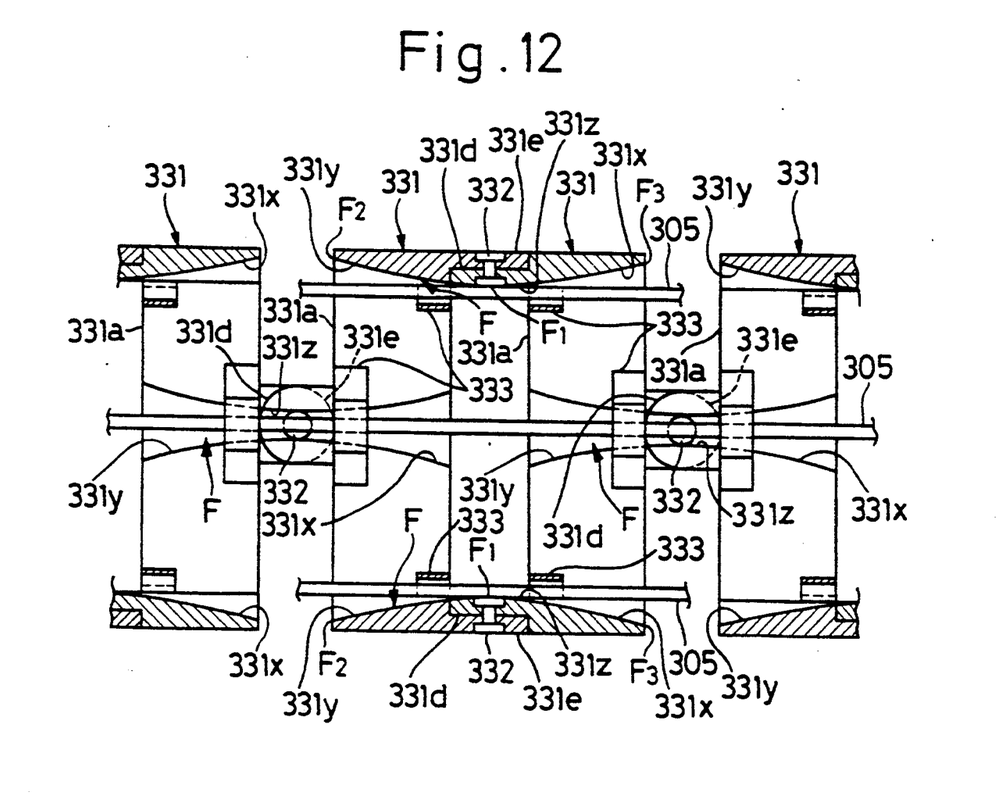
FIG. 12 is a view similar to FIG. 2, but showing a modified bending device using four operating wires.

FIG. 12 shows a bending device which can be bent in four directions. A segment 331 includes a tubular portion 331a, a pair of first connecting portions 331d which are formed on and extend axially from one end of the tubular portion 331a, and are circumferentially spaced 180° from each other, and a pair of second connecting portions 331e which are formed on and extend axially from the other end of the tubular portion 331a, and are circumferentially spaced 180° from each other, and are circumferentially spaced 90° from the first connecting portions 331d. The pair of first connecting portions 331d of any one of the segments 331 overlap the pair of second connecting portions 331e of its adjoining segment 331, respectively, and are pivotally connected by respective rivets (pintles) 332 to these second connecting portions 331e, respectively. The first connecting portion 331d is disposed inwardly of the second connecting portion 331e. Four guide members 333 for guiding four operating wires 305, respectively, are mounted respectively on those portions of the inner peripheral surface of the tubular portion 331a disposed in registry respectively with the first connecting portions 331d and the second connecting portions 331e in the circumferential direction. The front ends of the four operating wires 305 are fixedly secured to either the above-mentioned tip or the foremost segment 331, and are circumferentially spaced 90° from one another. A pair of first grooves 331x are formed respectively in those portions of the inner peripheral surface of the tubular portion 331a which are disposed in registry respectively with the pair of first connecting portions 331d in the circumferential direction. Similarly, a pair of second grooves 331y are formed respectively in those portions of the inner peripheral surface of the tubular portion 331a which are disposed in registry respectively with the pair of second connecting portions 331e in the circumferential direction. The distance between the bottom surface of the first groove 331x and the axis (centerline) of the tubular portion 331a is increasing progressively toward the right end (FIG. 12) of the tubular portion 331a. The distance between the bottom surface of the second groove 331y and the axis of the tubular portion 331a is increasing progressively toward the left end of the tubular portion 331a. A third shallow groove 331z is formed in the inner surface of the first connecting portion 331d. The bottom surface of each first groove 331x in any one of the segments 331 is generally continuous with the bottom surface of the corresponding second groove 331y in its adjoining segment 331 via the bottom surface of the third groove 331z, so that the bottom surfaces of these grooves 331x, 331y and 331z jointly constitute a wire guide surface portion F. The wire guide surface portion F is in the shape of an arc, and the distance between its center $F_1$ and the axis (centerline) of the bending device (the axis of the tubular portion 331a) is smaller than the distance between each of the opposite ends $F_2$ and $F_3$ of the wire guide surface portion F and the axis of the bending device. The radius of curvature of the wire guide surface portion F is equal to or smaller than the radius of a circle on which the centers $F_1$ of the wire guide surface portions F lie when the bending device is bent to the maximum degree.

In the case of using four operating wires, the wire guide members and the wire guide surface portions may be circumferentially spaced 45° from the pair of first connecting portions and the pair of second connecting portions.

The present invention can be applied to a bending device using a single operating wire. The segment may be of a semi-tubular shape, in which case a series of semi-tubular segments are connected together in such a manner that the segments are directed alternately in opposite directions.

The wire guide surface portion may not be in the shape of an arc. For example, the central portion of the wire guide surface portion may be different in radius of curvature from the opposite end portions of the wire guide surface portion. The radius of curvature of the wire guide surface portion may be increasing or decreasing progressively from its central portion toward its opposite ends.

What is claimed is:

1. A bending device comprising:
   (a) a number of segments arranged in a row along a longitudinal axis of the bending device, any two adjacent ones of said segments being pivotally connected together, each of said segments having an arcuate portion disposed around the longitudinal axis of the bending device, a pair of first connecting portions extending axially from one end, and a pair of second connecting portions extending axially from the other end, wherein said first connecting portions are circumferentially spaced 180° from each other, said second connecting portions are circumferentially spaced 180° from each other, and are disposed in registry with said first connecting portions, respectively, and wherein said pair of first connecting portions of any one of said segments overlap said pair of second connecting portions of its adjoining segment, and are pivotally connected by respective pintles to said second connecting portions, each of said segments further having guide means provided on an inner side of said arcuate portion and circumferentially spaced 90° from said first connecting portions;
   (b) an operating wire extending through said segments along the longitudinal axis of the bending device, said operating wire having a distal end substantially fixed relative to a foremost one of said segments, said operating wire guided by said guide means, said bending device bending when a proximal end of said operating wire is subject to a pulling force, and that portion of an inner peripheral surface of said segment along which said operating wire extends serving as a wire guide surface portion so that the section of contact of said wire guide surface portion with said operating wire becomes longer as the degree of bending of the bending device increases; and
   (c) said wire guide surface portion forming an inwardly-convex, continuous curved line, the distance between said wire guide surface portion and the longitudinal axis of said bending device progressively increasing from a central portion of said wire guide surface portion toward opposite ends of said wire guide surface portion.

2. A bending device according to claim 1, in which the distance between the central portion of said wire guide surface portion and the center of a circle on which the centers of said wire guide surface portions lie when the bending device is bent to the maximum degree is not less than the distance between each of the opposite ends of said wire guide surface portion and the center of said circle.

3. A bending device according to claim 1, in which the radius of curvature of said wire guide surface portion of said segment is not more than a radius of curvature of a circle circumscribing said wire guide surface portions of said number of segments of the bending device bent to the maximum degree.

4. A bending device according to claim 1, in which the radius of curvature of said wire guide surface portion of said segment is constant over an entire length thereof.

5. A bending device according to claim 1, wherein said segment includes a tubular portion, part of which serves as said arcuate portion.

6. A bending device according to claim 5, in which an outer peripheral surface of said segment is a complete cylindrical surface, a groove being formed in an inner peripheral surface of said segment and extending axially of said segment, and a bottom surface of said groove serving as said wire guide surface portion.

7. A bending device comprising:
(a) a number of segments arranged in a row along a longitudinal axis of the bending device, any two adjacent ones of said segments being pivotally connected together, each of said segments having an arcuate portion disposed around the longitudinal axis of the bending device, a pair of first connecting portions extending axially from one end, and a pair of second connecting portions extending axially from the other end, wherein said first connecting portions are circumferentially spaced 180° from each other, said second connecting portions are circumferentially spaced 180° from each other, and are disposed in registry with said first connecting portions, respectively, and wherein said pair of first connecting portions of any one of said segments overlap said pair of second connecting portions of its adjoining segment, and are pivotally connected by respective pintles to said second connecting portions, each of said segments further having guide means provided on an inner side of said arcuate portion and circumferentially spaced 90° from said first connecting portions;
(b) an operating wire extending through said segments along the longitudinal axis of the bending device, said operating wire having a distal end substantially fixed relative to a foremost one of said segments, said operating wire guided by said guide means, said bending device bending when a proximal end of said operating wire is subject to a pulling force, and that portion of an inner peripheral surface of said segment along which said operating wire extends serving as a wire guide surface portion so that the section of contact of said wire guide surface portion with said operating wire becomes longer as the degree of bending of the bending device increases; and
(c) said wire guide surface portion forming an inwardly-convex, continuous curved line, the distance between said wire guide surface portion and the longitudinal axis of said bending device progressively increasing from a central portion of said wire guide surface portion toward opposite ends of said wire guide surface portion, wherein said segment includes a tubular portion, part of which serves as said arcuate portion and wherein each of said segments has a uniform thickness and a circular cross-sectional shape over an entire length thereof, the diameter of each of said segments progressively increasing from its axially central portion toward its opposite ends.

8. A bending device comprising:
(a) a number of segments arranged in a row along a longitudinal axis of the bending device, any two adjacent ones of said segments being pivotally connected together, each of said segments having an arcuate portion disposed around the longitudinal axis of the bending device, a pair of first connecting portions extending axially from one end, and a pair of second connecting portions extending axially from the other end, wherein said first connecting portions are circumferentially spaced 180° from each other, said second connecting portions are circumferentially spaced 180° from each other, and are disposed in registry with said first connecting portions, respectively, and wherein said pair of first connecting portions of any one of said segments overlap said pair of second connecting portions of its adjoining segment, and are pivotally connected by respective pintles to said second connecting portions, each of said segments further having guide means provided on an inner side of said arcuate portion and circumferentially spaced 90° from said first connecting portions;
(b) an operating wire extending through said segments along the longitudinal axis of the bending device, said operating wire having a distal end substantially fixed relative to a foremost one of said segments, said operating wire guided by said guide means, said bending device bending when a proximal end of said operating wire is subject to a pulling force, and that portion of an inner peripheral surface of said segment along which said operating wire extends serving as a wire guide surface portion so that the section of contact of said wire guide surface portion with said operating wire becomes longer as the degree of bending of the bending device increases; and
(c) said wire guide surface portion forming an inwardly-convex, continuous curved line, the distance between said wire guide surface portion and the longitudinal axis of said bending device progressively increasing from a central portion of said wire guide surface portion toward opposite ends of said wire guide surface portion, wherein said segment includes a tubular portion, part of which serves as said arcuate portion and wherein each of said segments has a uniform thickness, only said wire guide surface portion projecting radially outwards relative to the remainder of said segment.

9. A bending device comprising:
(a) a number of segments arranged in a row along a longitudinal axis of the bending device, any two adjacent ones of said segments being pivotally connected together, said segment including a tubular portion, said segment having a pair of first connecting portions extending axially from one end of said tubular portion, said first connecting portions being circumferentially spaced 180° from each other, said segment having a pair of second connecting portions extending axially from the other end of said tubular portion, said second connecting portions being circumferentially spaced 180° from each other, and being circumferentially spaced 90° from said first connecting portions, said pair of first connecting portions of any one of said segments overlap said pair of second connecting portions of its adjoining segment, respectively, and being pivotally connected by respective pintles to these second connecting portions, respectively, and four guide means being provided on an inner side of said segment, and being disposed in registry respectively with said first and second connecting portions in a direction of the circumference of said segment; and (b) four operating wires extending through said segments along the longitudinal axis of the bending device, said four operating wires having their distal ends substantially fixed relative to a foremost one of said segments, said four operating wires being guided by said four guide means, respectively, the bending device being bent when a proximal end of each of said operating wires is subjected to a pulling force;

(c) inner peripheral surfaces of said tubular portions of any two adjacent ones of said segments cooperating with an inner surface of an inner one of said overlapped first and second connecting portions to form a substantially continuous wire guide surface portion along which said operating wire extends, said wire guide surface portion forming an inwardly convex, substantially continuous curved line, and the distance between said wire guide surface portion and the longitudinal axis of the bending device increasing progressively from a central portion of said wire guide surface portion toward opposite ends of said wire guide surface portion.

* * * * *